United States Patent [19]

Baidwan et al.

[11] 4,299,238
[45] Nov. 10, 1981

[54] VENTED PISTON AND PUSH-ROD SUBASSEMBLY FOR USE IN A SYRINGE BARREL

[76] Inventors: Balinderjeet S. Baidwan, 1236 Garfield; Dean H. Iwaski, 1465 Monroe St., both of, Denver, Colo. 80206

[21] Appl. No.: 162,329

[22] Filed: Jun. 24, 1980

[51] Int. Cl.³ .............................................. A61B 5/14
[52] U.S. Cl. ................................. 128/763; 128/218 P
[58] Field of Search .................. 128/763, 766, 218 P, 128/218 PA, 215, 276, 234, 220

[56] References Cited

U.S. PATENT DOCUMENTS

| | | | |
|---|---|---|---|
| 1,563,627 | 12/1925 | Hein | 128/200 |
| 1,799,463 | 4/1931 | Hein | 128/220 |
| 1,961,023 | 5/1934 | West | 128/218 P |
| 3,566,859 | 3/1971 | Schwartz | 128/218 M |
| 3,699,961 | 10/1972 | Szpur | 128/218 M |
| 4,206,768 | 6/1980 | Bailey | 128/763 |

FOREIGN PATENT DOCUMENTS 1212565 11/1970 United Kingdom ............ 128/218 P

*Primary Examiner*—John D. Yasko
*Attorney, Agent, or Firm*—Edwin L. Spangler, Jr.

[57] ABSTRACT

This invention relates to an improved vented syringe of a type ideally suited to the taking of blood samples for blood gas analysis and, more particularly, to a novel piston and push-rod subassembly for use therewith wherein the rubber piston on the tip of a rigid push-rod cooperate with one another to vent air out the rear end of the syringe barrel while trapping that contaminated portion of the blood sample that came in contact with the vented air inside the piston's hollow interior. Specifically, the piston is encircled on both ends by annular ribs sized for sliding contact with the interior of the syringe barrel, the upstream rib of the two having slits therein to pass both air and blood to a medial portion of reduced cross section while the downstream one maintains a continuous annular fluid and air-tight seal. A slit in the medial section admits the blood and air passing the upstream rib to the hollow interior of the piston when, with the piston subassembly in a passive state, a fluid-tight seal effective to prevent the passage of blood rearwardly out of the hollow interior of the piston is established that will freely pass air. These same elements of the piston subassembly cooperate when the latter is forcefully urged in either direction to establish an annular seal between opposed surfaces of the piston and push-rod tip that is both liquid and air-tight.

14 Claims, 7 Drawing Figures

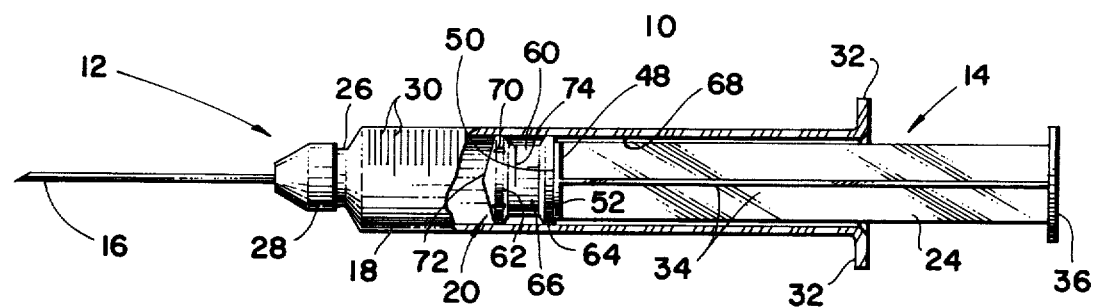
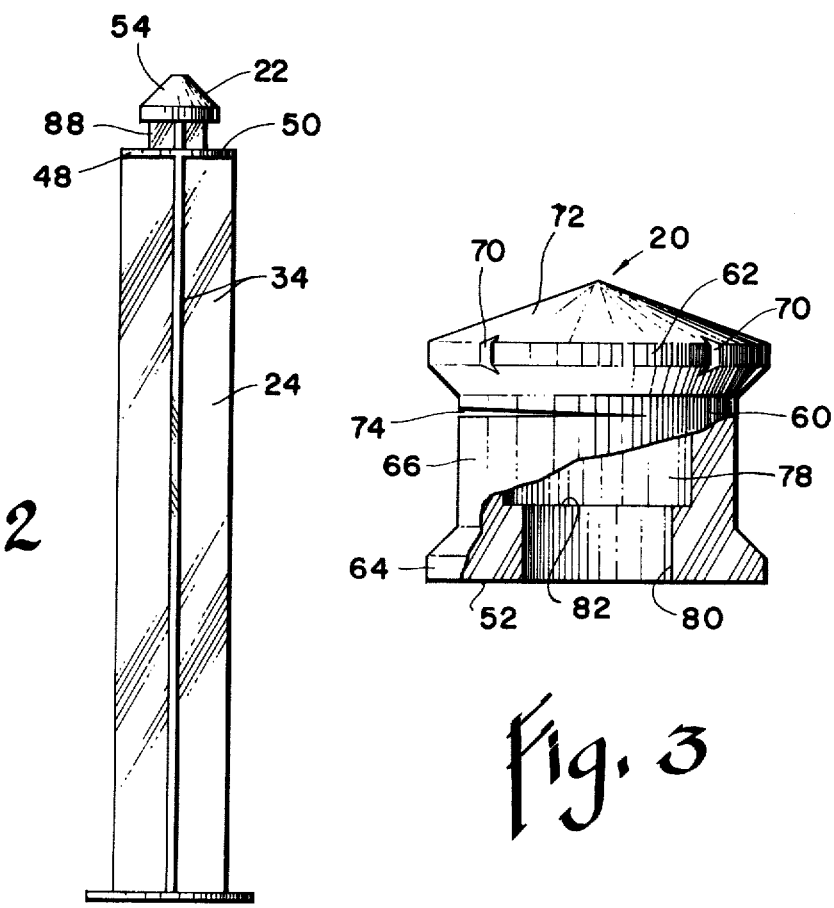

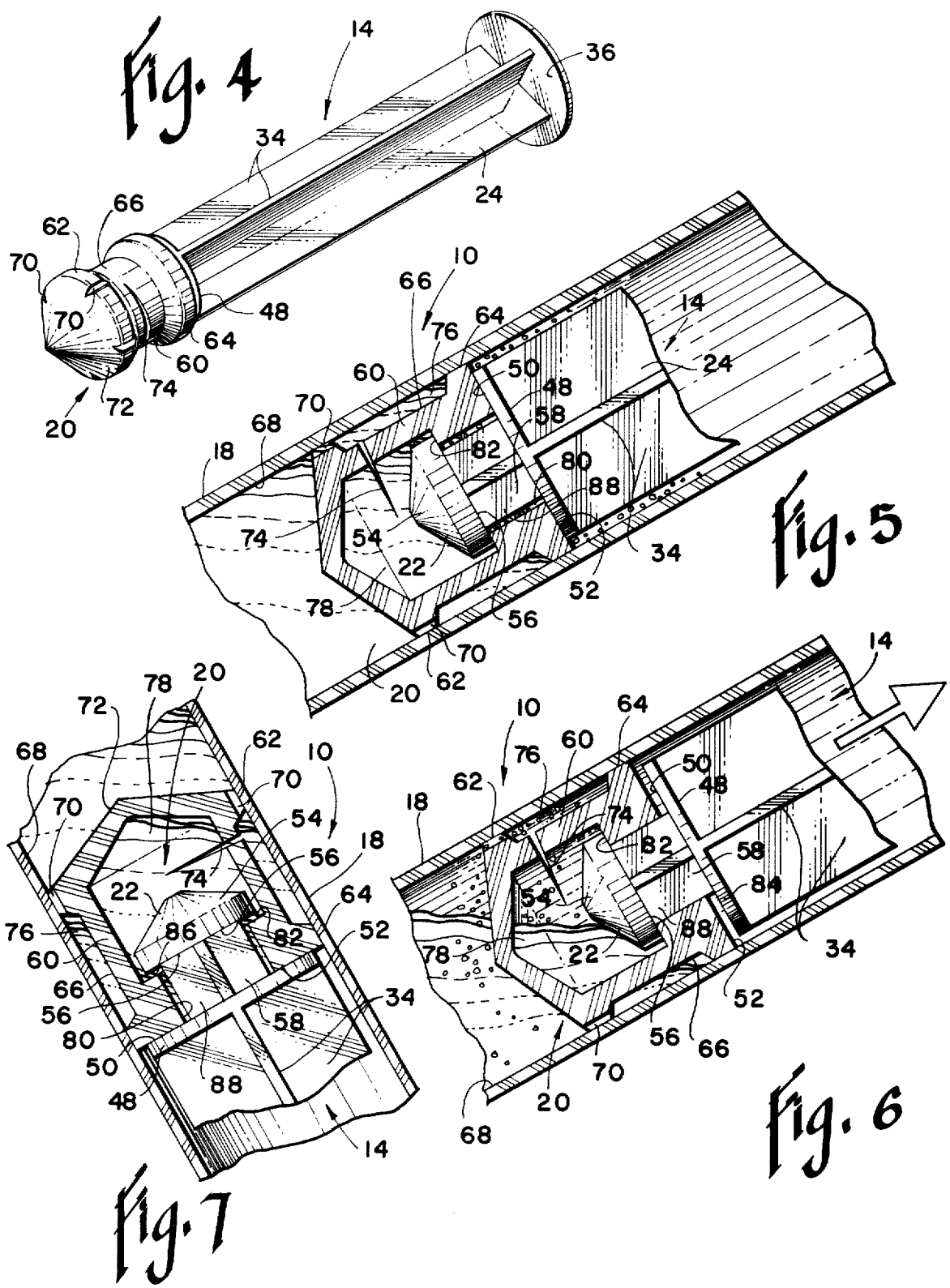

VENTED PISTON AND PUSH-ROD SUBASSEMBLY FOR USE IN A SYRINGE BARREL

For nearly twenty years now, the medical profession has accepted a gas analysis of a person's arterial blood as a reliable indication of the condition of their respiratory system. The pH, so-called carbon dioxide and oxygen gas "tensions" become important as means for establishing procedures that meet the needs of patients with either respiratory or metabolic disorders, or both.

Arterial blood specimens for use in making these determinations are customarily taken from the radial, brachial or femoral arteries. Extreme care must be taken in obtaining the sample to insure, if possible, that it does not become contaminated with air because such contamination is a source of significant error. The other source of error is that of dilution occasioned by the introduction of a liquid anticoagulant into the syringe which cannot, under most circumstances, be discharged therefrom completely and what remains, therefore, ends up diluting the blood sample. Other significant problems have been such things as having to use large gauge needles to get the required arterial blood pressure into the syringe barrel that is required to retract the plunger unassisted, the need to take a great deal more blood from the patient than is actually required for the blood gas test just to lessen the effects of sample dilution, the inability of some prior art syringes to accommodate abnormal conditions such as low arterial pressure and the like and, most significant, the almost universal problem of sample contamination and recontamination with trapped air.

Pre-filling the syringe with liquid heparin as an anticoagulant has the advantage of lessening, if not completely eliminating the air contamination problem, however, it is solely responsible for sample dilution which, in the case of small 5 to 10 cc syringes, can be shown to run as 17% in a 1 cc sample due to the liquid that remains trapped in the needle, the hub thereof and the neck of the syringe barrel where the piston cannot reach even when fully extended. Unfortunately, such dilution results in a false (unusually low) $CO_2$ reading and, since blood pH is the negative log of the $CO_2$ concentration, it has a pronounced deleterious effect upon two of the three directly measured parameters, only the oxygen concentration being independent thereof.

The usual solution for the dilution problem is to just simply take a larger sample, say 3 or 4 cc's, despite the fact that 1 cc or less would be quite adequate since the blood gas analysis machines require less than a third of a cc. To take a sample of this size rapidly so as to minimize the leaking of blood beneath the skin (hemotoma), a large gauge needle is used despite the resultant trauma to the punctured site. In some seriously ill patents whose arterial blood must be analyzed at frequent intervals, the trauma of being repeatedly punctured with a hypodermic needle is of no small significance to say nothing of the loss of blood, probably close to 90% of which is merely discarded.

Seemingly the obvious answer to the dilution problem is one of using an anticoagulant in the dry as opposed to the liquid state and this is, as a matter of fact, being done more and more. This procedure too, however, has its shortcomings because without the voids in the syringe being pre-filled with liquid, they are left filled with air and it contaminates the sample to the extent that the oxygen readings become erroneous and also unpredictably so which is not necessarily true with the dilution error. In other words, one can fairly accurately predict the dilution error just knowing the size of the sample taken and the size of the syringe. Such is not the case with oxygen contamination.

The prior art attempts at overcoming the foregoing problems have met, with only limited success. One of the few vented blood gas syringes is that which forms the subject matter of U.S. Pat. No. 4,133,304. Among other features, it has no plunger but instead uses a sample collection tube with a plug in both ends, the one in the rear end having holes through it filled with string that will pass air but block the passage of blood. This syringe constituted a considerable step forward in the art because it was the first to use dry heparin as an anticoagulant thus solving the dilution problem and it also enabled a small gauge needle to be used. On the other hand, the lack of a plunger caused certain problems of its own. Specifically, with no way of aspirating blood into the syringe, sometimes the patent's arterial pressure becomes inadequate to fill it and, therefore, a partially-filled tube exists which may not contain an adequate sample but, in any event, it is definately not an anaerobic one.

Even more important than the above, however, is the inability to expel clots from the needle which, if present, quickly clog up the small capillaries in the testing machine. Moreover, the small gauge needle is much more prone to clotting problems than the large one, especially since it is not pre-coated with dry heparin or some such dry anticoagulant.

One other shortcoming remains, and that is the problem of getting the sample adequately mixed prior to its introduction into the testing apparatus. The red cells in the blood settle out of the plasma in which they are suspended, thus necessitating that the sample be mixed while in the syringe. This is usually done by merely laying the syringe in the palm of the hand and rolling it back and forth. While this is no problem with the large barreled syringes, the aforementioned plungerless one has such a small diameter collection tube that adequate mixing of the sample cannot be accomplished in the conventional way; therefore, a steel ball is housed inside the blood-collection tube that can be moved axially back and forth with a magnet on the outside thereof.

Another of the vented syringes is that which is marketed under the trademark "OMNISTIK" by Medical Products, Inc. of Englewood, Colorado. It incorporates a plunger with three circumferential ribs, the end ribs of which lie in sealed contact with the barrel while the middle one has a notch therein, but across all three of which lies a filament attached to the push-rod. The incoming sample does not have to retract the plunger which is pre-set to the desired sample volume. The incoming blood pushes the air in the barrel ahead thereof and through the gaps in the ribs created by the filament. Once the syringe barrel is filled to the pre-set volume, the push-rod is rotated to retract the string which winds around the latter and allows the end ribs to reseal, thus giving an anaerobic sample.

Leakage past the piston seems to be the principal problem with this syringe since the end ribs become permanently dented to the point where they fail to reseal if the unit is not used fairly soon after manufacture. This same leaking problem caused by permanently dented ribs may, on occasion, prevent aspiration of a sample in case the patient has insufficient arterial pressure to fill the syringe. Unfortunately, the string cannot be laid across the ribs just prior to use because, in so doing, the sterility of the system is destroyed.

Another problem with this syringe is that of having to orient the string and air vents on top to keep from trapping a bubble of air in front of the piston up at the top. This air bubble is a real problem because, first of all, it destroys the anaerobic nature of the sample. Also, in attempts to expel the air bubble, blood will leak past the piston along the string at which point it can be a source of contamination for the technician.

One remaining shortcoming of this syringe is the difficulty experienced in telling whether the string has been retracted or not. Once the syringe has been filled with blood and blood surrounds the piston all the way back to the rear end rib, it is almost impossible to tell whether the string has been retracted or not. Should this be the case and the technician attempts to advance the plunger with the vent still open in order to introduce the sample into the testing apparatus, the sample will exit out the rear end to the syringe and thus constitute a source of contamination for the technician.

About the only other vented syringe is the so-called "Pharmaseal" syringe made by Pharmaseal Laboratories in Glendale, California. It uses a flexible plastic tube having a socket at its forward end and a semi-permeable plug at its rear end that will pass air while blocking the blood. An external clamp is used in place of a piston which can be slid along the outside of the tube to eject the sample into the testing apparatus. It cannot, however, be used to aspirate blood and, therefore, the syringe cannot be used under emergency conditions where the patient has little or no arterial pressure such as, for example, in the case of cardiac arrest.

The highly flexible nature of the tube has proven to be a source of difficulty in ejecting the sample into the testing machine by advancing the clamp because the tube bends. The solution to this problem has been to provide a stand or bench to lay the barrel upon while ejecting the sample thus eliminating any chance of the tube bending.

Another factor is that since the clamp is never completely tight, it becomes very difficult to rid the sample of clots. If, perchance, insufficient blood has been expelled to insure that all the clots have been eliminated when the clamp reaches the forward end of the tube, it cannot be reset and started over because all the blood therebehind has become contaminated with air.

These factors plus the need to use the magnet and ball mixing system with a sample a good deal larger than that required by certain of the other vented systems render the syringe less than completely satisfactory for its intended purpose. Among its advantages are the use of dry heparin thus eliminating the dilution problem and, of course, the effective venting of the air contained within the tube behind the clamp.

Other syringes are those forming the subject matter of U.S. Pat. Nos. 2,882,899; 3,147,753; 3,164,303; 3,674,181; 3,941,129; 3,874,382 and 4,159,713. Of these, only the Marks, et al patent shows a vented piston and it is wholly unsuitable for taking an anaerobic sample nor is it intended to do so.

It has now been found in accordance with the teaching of the instant invention that these and others shortcomings of the prior art vented blood gas syringes can, in large measure, be overcome by the simple, yet unobvious expedient of slitting the forward annular rib of the elastic piston to pass both blood and air to the medial section thereof, admitting both blood and air to the hollow interior of the piston through a slit in its medial section, and trapping the air-contaminated blood inside the piston while venting the air therefrom past a liquid-tight, but not an air-tight annular seal. The foregoing takes place in what will be denominated here as the "passive" condition of the syringe wherein the piston subassembly housed inside the barrel is being urged neither into extended or retracted position. The instant syringe also includes the capability of forming a seal which is both liquid and air-tight when the piston subassembly is forceably urged in either direction.

The syringe handles the dilution problem in the same manner as certain of the prior art syringes by using a dry anticoagulant. In addition, however, it needs no pre-alignment, can be used with a small gauge needle because very little arterial pressure is required to vent the trapped air past the piston and, most important of all, it retains its full aspirating and clot-expulsion capability. If, for instance, the patient's arterial pressure is insufficient to fill the syringe barrel to the pre-selected volume, one need only aspirate blood from the patent and then seal the needle before advancing the piston past the blood that has been taken, all without having to enter the patient's artery a second time. Expelling clots and introducing the sample taken into the testing apparatus also provides no problem even with a minimum sample of, say a single cc or less.

It is, therefore, the principal object of the present invention to provide a novel and improved vented blood gas syringe.

A second objective is the provision of a device of the class described which requires no pre-alignment or difficult manipulation or special preparation other than to set it to accept a pre-selected sample volume and insure the adequate coating of all its interior parts with the dry anticoagulant.

Another object of the within described invention is to provide a blood gas syringe that retains the full aspirating and clot-expulsion capability.

Still another objective is that of providing a vented blood gas syringe that fills by itself under conditions of minimal arterial pressure.

An additional object is to provide a syringe of the type aforementioned that is operated just like the prior art conventional unvented syringe and, therefore, does not require the technicians using same to learn any new manipulative techniques.

Further objects are to provide a syringe that is simple, easy to use, inexpensive, versatile, virtually foolproof, compact, rugged and fully compatible with existing blood gas testing machines.

Other objects will be in part apparent and in part pointed out specifically hereinafter in connection with the description of the drawings that follow, and in which:

FIG. 1 is a side elevation, portions of which have been broken away and shown in sections revealing the blood gas syringe of the present invention in its entirety;

FIG. 2 is an elevation to a somewhat enlarged scale showing the push-rod with its intergrally-formed head that forms a part of the piston subassembly;

FIG. 3 is a still further enlarged elevation of the piston and push-rod subassembly;

FIG. 4 is a fragmentary perspective to a scale somewhere between that of FIG. 2 and FIG. 3 showing the piston in assembled relation on the head of the push-rod;

FIG. 5 is a fragmentary diametrical section to the same scale as FIG. 3 showing the seal-forming elements of the syringe in the passive state and filled with blood;

FIG. 6 is a fragmentary view in diametrical section like FIG. 5 and to the same scale except that it shows the piston subassembly being forceably retracted to aspirate blood into the barrel; and, FIG. 7 is a fragmentary view in diametrical section like FIG. 5 and FIG. 6 and to the same scale but differing therefrom in that the piston subassembly is shown activated is a forward direction to expel the sample.

Referring next to the drawings for a detailed description of the present invention and, initially, to FIG. 1 for this purpose, reference numeral 10 has been selected to broadly designate the syringe while numerals 12 and 14 similarly refer to the barrel and piston subassemblies, respectively, thereof. Barrel subassembly 12 has, for purposes of the present description been considered to include the hypodermic needle 16, since both it and the barrel 18, to which it is attached are of a construction well-known in the art. Piston subassembly 14, on the other hand, includes a unique piston which has been broadly designated by reference numeral 20 and which detachably fastens onto the head 22 (FIGS. 2, 5 and 6) of pushrod-type plunger 24, the latter like the barrel and needle, being of more or less standard construction. Barrel 18 is necked-down at the front end thereof as indicated at 26 to detachably accept the hub 28 on the rear end of the needle. The barrel is also provided with volumetric indicia 30 and fingerholds 32 at its rear end.

Pushrod-type plunger 24, in the particular form shown, has the rod formed from crossed integral webs 34 of a width just slightly less than the inside diameter of the syringe barrel 18, the two cooperating in telescoped relation to keep the piston 20 axially aligned. The rear end of the rod is provided with an integrally-formed thumbrest 36 while head 22 is separated from rod-forming webs 34 by annular flange 48 that defines a forwardly-facing shoulder 50 against which the rear end 52 of piston 20 abuts and cooperates with to define a continuous annular fluid and liquid-tight seal when the plunger is pushed forwardly in the barrel as shown in FIG. 7.

The head 22 of the pushrod-type plunger 24 is most clearly revealed in FIGS. 2, 5 and 6 where it will be seen to include an axially-extending frustoconical tip 54 having a rearwardly-facing shoulder 56 spaced forwardly of shoulder 50 by a neck 58. The width of neck 88 is substantially less than the diameter of tip 22 so as to leave shoulder 56 exposed for a reason that will be set forth shortly.

The novel aspects of the syringe forming the subject matter hereof are, for the most part at least, confined to piston 20, although certain important dimensional relationships exist between it and the head 22 upon which it is detachably mounted. Before considering the latter, however, it will be well to examine the structure of the piston 20 itself for which purpose reference will be had to FIGS. 1, 3, 4, 5, 6 and 7.

This piston 20 is molded from rubber or some other elastic material in the manner common to such syringe pistons and it includes a hollow one-piece body 60 having an upstream annular rib 62 on the front end and a downstream annular rib 64 on the rear end separated by a medial portion 66 of reduced cross section. Both ribs 62 and 64 are sized to engage the inside cylindrical surface 68 of the barrel with a free-sliding fit, that of the latter being fluid-tight while the former is not due to the presence of at least one slit 70 in its periphery. If but a single slit 70 is used, it must be positioned at or near the uppermost point in the syringe barrel to insure that no air is trapped ahead of the piston as will be explained in greater detail presently in connection with FIG. 6; therefore, in the preferred embodiment illustrated, a plurality of such slits are spaced around the periphery of rib 62 to insure that at least one is, in fact, located near the zenith of the barrel.

The front end or tip 72 of the piston is shown to have a shallow conically-shaped surface although its shape is relatively insignificant so long as it is smooth and contains no crevices or other interstices that could trap and retain bacteria and other contaminants that would interfere with its being properly sterilized before being packaged. It is also worthy of note that the wiping surfaces of ribs 62 and 64 that engage the cylindrical surface on the inside of the barrel are both reasonably broad as opposed to a thin knife-edged surface which is more difficult to seal. Here again, neither the width nor the cross section of these ribs is particularly critical so long as they perform their intended functions but, on the other hand, there is no real reason for departing from the basic cylindrical surfaces shown either. About the only remaining feature clearly visible on the outside of piston 20 is slit 74 in medial portion 66 that connects the annular space 76 therearound and in between the ribs with fluid collection chamber 78 in the hollow interior thereof. The size of this chamber along with the entryway 80 thereto in relation to the head 22 of the piston subassembly 14 is most clearly revealed in FIGS. 3, 5, 6 and 7 to which detailed reference will next be made.

Chamber 78 in the hollow interior of piston 20 is considerably oversized in relation to the tip 54 of the push-rod head which is housed therein thus defining a pocket within which to confine the contaminated blood that both lies ahead of and extends all the way around the latter. This chamber remains open to receive both blood and air entering through slit 74 regardless of whether the push-rod is being urged forwardly against the piston 20 or is being pulled away from the latter or is merely left free to find its own orientation relative thereto. The more critical dimension is the length measured axially of the entryway 80 into fluid collection chamber 78 which must be essentially the same as that of neck 58 measured between opposed surfaces 50 and 56. A forwardly-facing annular shoulder 82 is located at the juncture between chamber 78 and the entryway 80 thereto which, in the relaxed condition shown in FIG. 5 is held by opposed mating surfaces 50 and 52 in annular fluid-tight, but not air-tight, relation up against rearwardly-facing shoulder 56. In other words, when the front end 50 of pushrod 24 rests, but is not forced, up snug against the rear end 52 of the piston, the relationship between opposed annular shoulders 56 and 82 will be such that any air within chamber 78 will pass freely therebetween under the influence of the higher than atmospheric arterial pressure of the blood therebehind. Once the air is past the tip 54 of the pushrod head, it is free to travel rearwardly along the neck 58 and exit the syringe barrel after passing between the aforesaid surfaces 50 and 52. These selfsame surfaces, on the other hand, cooperate when wetted with the blood entering cavity 78 to form a fluid-tight annular seal that will not let any blood escape yet will still pass air. In the free-floating condition of FIG. 5, therefore, there is a fluid-tight seal established at the interface between opposed annular surfaces 52 and 56 effective to prevent the flow of blood past the piston but not the air pushed rearwardly by the latter. By way of contrast, if one were to manually retract the piston subassembly 14 so as to aspirate blood into the syringe (see FIG. 6), a different condition is called for in that both a fluid-tight and an air-tight annular seal must exist at the interface between surfaces 56 and 82 because, otherwise, air could flow forwardly past the piston 20 from the atmosphere thus equalizing the pressure on both ends thereof and preventing the establishment of the negative pressure ahead of the piston necessary to suck blood into the barrel. When operating in the aspirating mode, a small gap 84 will be created between normally-mated surfaces 50 and 52 caused by the slight compression of the rubber piston behind shoulder 56 when the latter is urged forcefully thereagainst. Conversely, when forcefully expelling blood from the syringe through the needle as shown in FIG. 7, the opposite condition exists, namely, a gap 86 is created between normally-mated surfaces 56 and 82 due to the front end 50 of the pushrod pressing against and slightly compressing the rear end 52 of the piston. At the same time, however, both a fluid-tight and an air-tight annular seal is established at interface 50-52 effective to prevent both the blood and air from leaking past the piston in a rearward direction. Note that the resultant gap 86 breaks the liquid seal at this point and both blood and air can enter the hollow areas 88 in the neck of the pushrod head but go no further.

With the foregoing as a background, the time has come to proceed with a detailed description of the actual operation of the vented syringe 10 of the present invention when used to take an anaerobic blood sample and reference will be made to FIGS. 5, 6 and 7 for this purpose, starting with FIG. 5.

To take a sample for arterial blood gas analysis, the sterile syringe is taken from its package, assembled and the interior of the barrel, its neck 26 and needle 16 are pre-coated in the usual manner with dry heparin as an anti-coagulant. Next, the pushrod 24 is actuated to preset the piston to receive the desired blood sample, say a cubic centimeter or thereabouts. While only 0.3 cc's are needed for analysis by the existing blood gas analysis machines in current use, enough excess blood should be collected to, first of all, insure that that which enters the syringe first and came in contact with the air inside the latter has passed behind the front rib 62 of the piston through slits 70 in its periphery and on into fluid-collection chamber 78 by means of slit 74 so that the blood thus contaminated will not be a part of the blood sample ultimately tested. In addition, enough excess blood must be taken to expel clots back out through the needle by actuating the plunger forwardly as shown in FIG. 7 once the sample has been taken. No excess over and above the foregoing requirements is needed because, as will be seen shortly, the sample taken is undiluted and is also anaerobic.

With the plunger and piston thus preset as seen in FIG. 5, the needle is placed in the patient's artery in accordance with techniques well-known in the medical profession. Even though only a small volume cc syringe is employed to take the sample, the traditional large (18 to 22 gauge) needle can be dispensed with in favor of a much smaller gauge one because, to begin with, arterial pressure is not required to retract the plunger as is the case in some of the prior art blood gas syringes. Moreover, since the instant syringe is vented and the air located between the incoming blood and piston can move out past the latter, arterial pressure is entirely adequate under most circumstances to fill the syringe even through a small gauge needle. It is worthy of note, however, that if a situation should occur in which arterial pressure is insufficient to fill the syringe barrel to the preselected volume, yet enough of a sample has been collected, the person taking the sample need only seal off the needle and advance the piston as shown in FIG. 7 to a point where all the air has been vented and the blood contaminated by the latter has entered fluid collection chamber 78 in the manner previously described. Some prior art blood gas syringes are unable to accommodate this condition.

An analogous, yet different, situation is the one where not enough blood has been taken to complete the analysis at the point where arterial pressure proves inadequate to complete the job. In this event the person taking the sample need only retract the plunger and aspirate more blood into the syringe barrel without removing the needle from the artery. By so doing, the previously described condition illustrated in FIG. 6 will exist where the rear or downstream annular rib 64 is in annular air and liquid-tight sealed engagement with the inside cylindrical surface 68 of the barrel 18 and, in addition, a similar air and liquid-tight annular seal is formed between mating annular surfaces 56 and 82 of the plunger tip and piston, respectively. An additional quantity of blood can thus be aspirated into the syringe to make up any deficiency in the sample. Once the retraction stroke of the piston subassembly 14 has terminated, a pressure gradient will still exist due to the negative pressure ahead of the piston that tries to extend the latter, therefore, the plunger will need to be held. This same pressure gradient will urge the piston toward the front end of the barrel thus maintaining both an air-tight seal and a fluid-tight seal at interface 56-82. If this were not the case, air could move forwardly past the piston breaking the vacuum ahead thereof. As it is, the vacuum remains and continues operative to aspirate blood from the patient despite the absence of adequate arterial pressure. Blood will continue to enter the barrel until the air pocket downstream thereof is compressed between the latter and the air-tight seal existing at interface 56-82 to a level where its pressure equalizes that downstream of the piston, whereupon, the further influx of blood will cease. Once this state of affairs exists, the end of the needle can be plugged and the plunger extended in the manner already described to vent the air and trap the contaminated blood in fluid collection chamber 78.

The usual situation is, of course, the one illustrated in FIG. 5 where the piston subassembly 14 is "passive" in the sense that it is neither being forcefully extended or retracted. In this condition, the arterial pressure alone is sufficient to fill the barrel and fluid collection chamber 78 with blood while, at the same time, purging the air from upstream of piston 20. Once the blood reaches the interface 56-82, the desired fluid-tight seal is established that prevents any blood from getting past the piston although air can still do so. The portion of the blood resident in chamber 78 is, of course, the contaminated portion that has been in contact with the air and which, for this reason, is to be excluded from the sample tested. Actually, the sample used for the blood gas analysis is taken from the front end of the syringe after the clots, if any, have been forceably expelled therefrom.

Mention has been made of the desirability of having more than one slit 70 in the peripheral edge of upstream rib 62. Looking at FIG. 5, it will be apparent that if only the slit 70 at the bottom of the piston were present and none at the top, an air bubble would be trapped at the top of the piston which would have no means of escape. Obviously, by merely reorienting the piston subassembly 14 to place slit 70 at or near the apex of the barrel, the problem can be avoided, however, one cannot rely upon the fact that such a procedure will always be followed; therefore, the simplest answer is to provide a plurality of such slits spaced at intervals around the periphery of rib 62 so that regardless of how the piston subassembly 14 is oriented, one will be at or very near the apex of the barrel. Furthermore, there is no functional sacrifice by using more than one slit and, if anything, the use of several facilitates the venting of air from the assembly.

Once the sample has been taken either using the passive piston technique illustrated in FIG. 5 which relies exclusively upon the patient's arterial pressure or, alternatively, the aspirating technique of FIG. 6 either alone or in combination with the passive one as previously explained, the procedure of FIG. 7 comes next. If any air is left in the barrel ahead of the piston, the latter must be advanced with the needle plugged to vent such air and trap the first-taken blood that has been in contact therewith in chamber 78. Under ordinary circumstances this will be unnecessary as the passive technique of FIG. 5 will have been used where all of the foregoing takes place automatically so to speak under the influence of arterial pressure alone. Either way, an undiluted anaerobic blood sample of something greater than the required 0.3 cc's is present in the barrel suitably treated with the solid anti-coagulant. The presence of a clot in the needle or elsewhere is a serious consequence to be avoided because it can plug up the testing apparatus thus requiring that the latter be completely disassembled and cleaned, a procedure that often requires several hours. Accordingly, before introducing the sample into the testing apparatus, the piston subassembly 14 is first extended as shown in FIG. 7 with the needle open to expel a portion of the sample taken to insure that all clots have been eliminated. Also, having previously vented the air, it needn't be vented through the needle as in certain of the prior art systems thus preventing contamination of the sample by passing air therethrough. With no dilution of the sample due to the presence of a liquid anti-coagulant that cannot be entirely eliminated from certain parts of the syringe like, for instance, the hub of the needle, it is unnecessary to take a large sample to effectively lessen the dilution factor. Instead, only the minimum sample need be taken which will provide the 0.3 cc's needed for the testing apparatus, that which will be discarded when clearing the system of clots, and the contaminated portion which stays in chamber 78. Arterial pressure is not required to retract the piston subassembly 14 and it, therefore, becomes fully adequate under normal conditions to purge the syringe of air even using a smaller than normal gauge needle.

What is claimed is:

1. In a syringe of the type having a hollow cylindrical barrel open at both ends and with its open front end adapted to receive a needle, the improved vented piston and push-rod subassembly for insertion into its open rear end in plug-forming relation thereto which comprises: a cup-shaped piston formed from an elastic material having a hollow interior with a rear-opening entryway bordered at the front end by a front forwardly-facing annular sealing surface and at the rear end by a rear rearwardly-facing annular sealing surface, said piston also having a continuous annular rib encircling same effective upon insertion into the barrel to form a fluid and air-tight seal in wiping contact therewith, said piston further including means for admitting both fluids and air into the hollow interior thereof ahead of said continuous annular rib, said means comprising a discontinuous rib spaced forwardly of the continuous one and a medial section of reduced cross section between said ribs with an opening therethrough; and, a push-rod terminating at its forward end in a necked-down head cooperating therewith to define a front rearwardly-facing annular sealing surface and a rear forwardly-facing annular sealing surface spaced therebehind, said head being sized for insertion through the entryway into the piston so as to form a plug therefor while cooperating therewith to define a fluid collection chamber within the hollow interior thereof, the front forwardly-facing annular sealing surface of said piston and the front rearwardly-facing annular sealing surface of said push-rod cooperating upon the application of a force to the latter in a direction to retract same to define a continuous annular fluid and air-tight seal therebetween effective to aspirate fluid into said barrel when mounted therein, the rear rearwardly-facing annular sealing surface of said piston and the rear forwardly-facing annular sealing surface of said push-rod also cooperating upon the application of a force to the latter in a direction to extend same to define a continuous annular fluid and air-tight seal therebetween effective to discharge fluid from the open front end of said barrel when in place therein, and all four of said sealing surfaces between said piston and push-rod cooperating when no force is applied to the latter in either direction to define a continuous annular fluid-tight seal between said front sealing surfaces effective to vent air rearwardly past the piston from the hollow interior thereof while retaining all fluids collected in its fluid collection chamber.

2. The subassembly as set forth in claim 1 wherein the axial spacing between the front and rear annular sealing surfaces of the piston and push-rod, respectively, is substantially the same.

3. The subassembly as set forth in claim 1 wherein the discontinuous rib comprises an annular rib having at least one slit in its periphery.

4. The subassembly as set forth in claim 1 wherein the front annular sealing surfaces are substantially coplanar.

5. The subassembly as set forth in claim 1 wherein the rear annular sealing surfaces are substantially coplanar.

6. The subassembly as set forth in claim 1 wherein the medial section is of a size and shape adapted to cooperate with the barrel when in place therein to leave a continuous annular gap therebetween.

7. The subassembly as set forth in claim 1 wherein the continuous and discontinuous ribs cooperate with one another to maintain the piston in coaxial relation within the barrel when in wiping contact therewith.

8. The subassembly as set forth in claim 1 wherein a fluid seal effective to stop the passage of fluid but ineffective to stop the passage of air is formed between the front annular sealing surfaces when the push-rod has no force applied thereto in either direction.

9. The subassembly as set forth in claim 1 wherein upon application of a force to the push-rod in a direction to retract same, a gap is created between the rear annular sealing surfaces ineffective to retain either fluids or air.

10. The subassembly as set forth in claim 1 wherein upon application of a force to the push-rod in a direction to extend same, a gap is created between the front annular sealing surfaces ineffective to retain either fluids or air.

11. The subassembly as set forth in claim 3 wherein the discontinuous rib includes a plurality of slits spaced around the periphery thereof.

12. The subassembly as set forth in claim 4 wherein the coplanar annular sealing surfaces are substantially normal to the axis of piston movement within the barrel.

13. The subassembly as set forth in claim 5 wherein the coplanar annular sealing surfaces are substantially normal to the axis of piston movement within the barrel.

14. The subassembly in accordance with claim 5 wherein all four of the annular sealing surfaces between the push-rod and piston are substantially coplanar and normal to the axis of movement of the piston within the barrel.

* * * * *